United States Patent [19]

Bernini

[11] Patent Number: 4,621,152

[45] Date of Patent: Nov. 4, 1986

[54] PROCESS FOR THE ENANTIOMERIC RESOLUTION OF MIXTURES OF D AND L-6-METHOXY-ALPHA-METHYL-2-NAPHTHALENEACETIC ACID AND RESOLVING AGENT FOR SAID PROCESS

[75] Inventor: Giuseppe Bernini, Milan, Italy

[73] Assignee: Secifarma S.p.A., Italy

[21] Appl. No.: 582,311

[22] Filed: Feb. 22, 1984

[30] Foreign Application Priority Data

Mar. 7, 1983 [IT] Italy ................................ 19936 A/83

[51] Int. Cl.$^4$ .............................................. C07B 57/00
[52] U.S. Cl. ................................. 562/401; 260/501.1; 562/466
[58] Field of Search ............................... 562/401, 466; 260/501.1

[56] References Cited

U.S. PATENT DOCUMENTS

| | | | |
|---|---|---|---|
| 3,646,118 | 2/1972 | Goffinet et al. | 562/401 |
| 3,651,106 | 3/1972 | Harrison | 562/401 X |
| 3,683,015 | 8/1972 | Dyson | 562/401 |
| 3,725,465 | 4/1973 | Stoeck et al. | 562/401 X |
| 4,246,164 | 1/1981 | Felder et al. | 562/401 X |

FOREIGN PATENT DOCUMENTS 1167445 8/1958 France .

Primary Examiner—Natalie Trousof
Assistant Examiner—Vera C. Clarke
Attorney, Agent, or Firm—Ostrolenk, Faber, Gerb & Soffen

[57] ABSTRACT

The invention relates to a process for the resolution of mixtures of D and L-6-methoxy-alpha-methyl-2-naphthaleneacetic acid in their respective antipodes.

L-threo(+)-2-amino-1-p-nitrophenyl-1,3-propandiol is proposed as new resolving agent.

7 Claims, No Drawings

PROCESS FOR THE ENANTIOMERIC RESOLUTION OF MIXTURES OF D AND L-6-METHOXY-ALPHA-METHYL-2-NAPHTHALENEACETIC ACID AND RESOLVING AGENT FOR SAID PROCESS

DESCRIPTION

The present invention refers to a process for preparing mixtures strongly enriched in the D-isomer or in the L-isomer from mixtures of D and L-6-methoxy-alpha-methyl-2-naphthaleneacetic acid.

More particularly, the process of the present invention refers to the use of L-threo(+)-2-amino-1-p-nitrophenyl-1,3-propandiol as an agent for enantiomeric resolution.

Several processes for the resolution of mixtures of D,L-6-methoxy-alpha-methyl-2-naphthaleneacetic acids are already known, amongst which we should like to recall the one disclosed in U.S. Pat. No. 3,683,015 which provides for the use of cinchonidine as the resolving agent.

In the Patent Publication DE-2,007,177, moreover, many other bases useful as enantiomeric resolving agents for mixtures of the above referred acids are suggested. In particular, D-threo-2-amino-1-p-nitrophenyl-1,3-propandiol is cited. This product is normally obtained by the resolution of D,L-threo-2-amino-1-p-nitrophenyl-1,3-propandiol and it is of considerable commercial value since it is used for preparing chloramphenicol.

It has now been found that the L-threo(+)-2-amino-1-p-nitrophenyl-1,3-propandiol isomer, which i.a. up till now did not have any industrial use (and thus did not have any commercial value), can be advantageously used for separating the optical antipodes of D,L-6-methoxy-alpha-methyl-2-naphthaleneacetic acid mixtures.

According to the process of the present invention, the enantiomeric resolution is carried out in an inert organic solvent selected in such a way that the solubility of the D-isomer salt of the acid to be resolved by means of the resolving agent is remarkably different from the solubility of the corresponding salt of the L-isomer. Obviously, if one wishes to separate the D-isomer, one will select a solvent in which the corresponding salt with the resolving agent has a solubility which is remarkably lower than that of the salt of the L-isomer.

Preferably, the salification of the mixture of the D and L acids with the resolving agent is carried out at high tempeature so that when the reaction mixture is cooled, the salt of the D-isomer with L-threo(+)-2-amino-1-p-nitrophenyl-1,3-propandiol will be crystallized out.

Many solvents are useful for the process of the present invention. In particular, alcohols and ketones are preferred. Even more particularly, methanol and acetone in their anhydrous condition or containing more or less large quantities of water are preferred.

According to the process of the present invention, the mixture of the D and L acid to be resolved is heated up to the reflux tempeature of the solvent, in the presence of L-threo(+)-2-amino-1-p-nitrophenyl-1,3-propandiol, till complete dissolution of the reagents.

After the reagents have dissolved in the solvent, the solution is allowed to cool. During this time, the solution can be seeded with some salt of the isomer acid to be separated, with the resolving base. The resulting crystalline precipitate is strongly enriched in the salt of the less soluble isomer.

The resulting crystalline precipitate is separated by filtration and, preferably, recrystallized. From these salts the free acid can be obtained by usual methods.

This invention is further illustrated by the following specific but not limiting examples.

EXAMPLE 1

15 g of D,L-6-methoxy-alpha-methyl-2-naphthaleneacetic acid is dissolved in 65 ml acetone at 50° C. To this solution, 8.25 g L-threo(+)-2-amino-1-p-nitrophenyl-1,3-propandiol is added. After slow cooling to ambient temperature, a raw salt is obtained which, after crystallization from 50 ml acetone, yields 9.5 g of a product substantially enriched in the salt of D-6-methoxy-alpha-methyl-2-naphthaleneacetic acid with L-threo(+)-2-amino-1-p-nitrophenyl-1,3-propandiol having the formula $C_{14}H_{14}O_3 \cdot C_9H_{12}N_2O_4$.

EXAMPLE 2

300 g of D,L-6-methoxy-alpha-methyl-2-naphthaleneacetic acid and 138 g of L-threo(+)-2-amino-1-p-nitrophenyl-1,3-propandiol are dissolved in 1800 ml of boiling methanol. After slow cooling to ambient temperature, 210 g of crystals of a product substantially enriched in the salt of L,6-methoxy-alpha-methyl-2-naphthaleneacetic acid with L-threo(+)-2-amino-1-p-nitrophenyl-1,3-propandiol having the formula $(C_{14}H_{14}O_3)_2 \cdot C_9H_{12}N_2O_4$ separates. The methanolic solution is taken off and to the residue 70 g of L-threo(+)-2-amino-1-p-nitrophenyl-1,3-propandiol and 1146 ml of acetone are added. The thus obtained mixture is heated until the solution is completed. After slow cooling, 182 of a crystalline product substantially enriched in the salt of D-6-methoxy-alpha-methyl-2-naphthaleneacetic acid with L-threo(+)-2-amino-1-p-nitrophenyl-1,3-propandiol is obtained, having the formula $C_{14}H_{14}O_9 \cdot C_9H_{12}N_2O_4$.

EXAMPLE 3

94.3 g of the salt of D-6-methoxy-alpha-methyl-2-naphthaleneacetic acid with L-threo(+)-2-amino-1-p-nitrophenyl-1,3-propandiol having the formula $C_{14}H_{14}O_3 \cdot C_9H_{12}N_2O_4$ is suspended in a mixture of 225 ml water, 26.4 g $H_2SO_4$ 41 Bé and 220 ml toluene. The mixture is heated until it is completely dissolved. The aqueous layer is separated and to the toluene solution 360 ml water containing 24.2 g NaOH is added.

The separated aqueous phase after being acidified with sulfuric acid yields 44.5 g of D-6-methoxy-alpha-methyl-2-naphthaleneacetic acid.

I claim:

1. A process for the enantiomeric resolution of D- and L-6-methoxy-α-methyl-2-naphthalene-acetic acid which comprises mixing the enantiomeric mixture with L-threo(+)-2-amino-1-p-nitrophenyl-1,3-propanediol in the presence of a solvent in which the resulting salified enantiomers have different solubilities.

2. A process according to claim 1 in which the solvent used is one in which the salified D-enantiomer has less solubility than the salified L-enantiomer and is acetone.

3. A process according to claim 2 in which the mixture of enantiomers and propanediol in the acetone is heated to dissolve the reagents and then the resulting solution is allowed to cool.

4. A process according to claim 3 in which the cooled crystalline salified D-enantiomer is separated from the reaction mixture.

5. A process according to claim 1 in which the solvent is one in which the salified L-enantiomer has less solubility than the salified D-enantiomer and is methanol.

6. A process according to claim 5 in which the mixture of enantiomers and propanediol in the methanol is heated to dissolve the reagents and then the resulting solution is allowed to cool.

7. A process according to claim 5 in which the cooled crystalline salified L-enantiomer is separated from the reaction mixture.

* * * * *